US00PP12148P2

(12) United States Plant Patent
van Noort

(10) Patent No.: US PP12,148 P2
(45) Date of Patent: Oct. 16, 2001

(54) GERANIUM PLANT NAMED 'JOLLY BEE'

(75) Inventor: Marcus Wilhelmus Gerardus van Noort, Warmond (NL)

(73) Assignee: Witteman & Co. 'Multiflora' B.V., Hillegom (NL)

( * ) Notice: Subject to any disclaimer, the term of this patent is extended or adjusted under 35 U.S.C. 154(b) by 0 days.

(21) Appl. No.: 09/484,660

(22) Filed: Jan. 18, 2000

(51) Int. Cl.[7] ..... A01H 5/00
(52) U.S. Cl. ..... Plt./324
(58) Field of Search ..... Plt./324

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Geranium plant named 'Jolly Bee', characterized by its large violet flowers with purple veins and light lavender centers; long flowering period; and good garden performance.

2 Drawing Sheets

BACKGROUND OF THE INVENTION

The present Invention relates to a new and distinct cultivar of Geranium plant, botanically known as *Geranium shikokianum×G. wallichianum,* and hereinafter referred to by the cultivar name Jolly Bee.

The new Geranium is a product of a planned and controlled breeding program conducted by the Inventor in Warmond, The Netherlands. The objective of the breeding program is to create new interspecific Geraniums that are winter-hardy with large violet and light lavender flowers.

The new cultivar originated from a cross by the Inventor between an unnamed selection of *Geranium shikokianum var. yoshiianum* as the female, or seed, parent with the *G. wallichianum* cultivar Buxton's Variety as the male or pollen parent. The cultivar Jolly Bee was discovered and selected by the Inventor in 1998 as a plant within the progeny of the stated cross in a controlled environment in Warmond, The Netherlands.

Asexual reproduction of the new cultivar by divisions taken at Warmond, The Netherlands, has shown that the unique features of this new are stable and reproduced true to type in successive generations.

In side-by-side comparisons conducted by the Inventor in Warmond, The Netherlands, the following differences between the new Geranium and the female parent, an unnamed selection of *G. shikokianum var. yoshiianum,* have been observed:

1. Plants of the new Geranium are more vigorous than plants of the unnamed selection of *G. shikokianum var. yoshiianum.*

2. Plants of the new Geranium are larger than plants of the unnamed selection of *G. shikokianum var. yoshiianum.*

3. Plants of the new Geranium and plants of the unnamed selection of *G. shikokianum var. yoshiianum* differ in flower color.

In side-by-side comparisons conducted by the Inventor in Warmond, The Netherlands, the following differences between the new Geranium and the male parent, the *G. wallichianum* cultivar Buxton's Variety, have been observed:

1. Plants of the new Geranium are larger than plants of the cultivar Buxton's Variety.

2. Flowers of plants of the new Geranium are larger than flowers of plants of the cultivar Buxton's Variety.

3. Plants of the new Geranium are more winter-hardy than plants of the cultivar Buxton's Variety.

SUMMARY OF THE INVENTION

Plants of the cultivar Jolly Bee have not been observed under all possible environmental conditions. The phenotype may vary somewhat with variations in environment such as temperature, light intensity, daylength, and fertilizer rate without, however, any variance in genotype.

The following traits have been repeatedly observed and are determined to be the unique characteristics of 'Jolly Bee'. These characteristics in combination distinguish 'Jolly Bee' as a new and distinct cultivar:

1. Large violet flowers with purple veins and light lavender centers.

2. Long flowering period.

3. Good garden performance.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Geranium.

The photograph at the top of the first sheet comprises a side perspective view of a typical flowering plant of 'Jolly Bee'.

The photograph at the bottom of the first sheet comprises a close-up view of a typical flower of 'Jolly Bee'.

The photograph at the top of the second sheet comprises a close-up view of typical leaves and flowers of 'Jolly Bee'.

The photograph at the bottom of the second sheet comprises a close-up view of a typical flower bud and a typical flower of 'Jolly Bee'. The age and the environmental conditions of the plant depicted in the photograph are the same as those described in the Detailed Botanical Description.

DETAILED BOTANICAL DESCRIPTION

The following observations, measurements and values describe about 20 week old plants of the new cultivar grown under outdoor conditions during the summer in Warmond, The Netherlands. Color references are made to The Royal Horticultural Society Colour Chart except where general terms of ordinary dictionary significance are used.

Botanical classification: *Geranium shikokianum*×*G. wallichianum* cultivar Jolly Bee.

Parentage:

*Female parent.*—*Geranium shikokianum var. yoshiianum,* not patented.

*Male parent.*—*Geranium wallichianum* cultivar Buxton's Variety, not patented.

Propagation:

*Type.*—By divisions.

*Time to produce a rooted liner.*—About 40 days during the spring in Warmond, The Netherlands.

*Rooting habit.*—Fleshy.

Plant description:

*Form.*—Flat, rounded, outwardly spreading.

*Usage.*—Perennial garden plant.

*Crop time.*—From cuttings, about 20 weeks are required to produce fully-grown flowering plants in 17-cm containers.

*Plant height* (*from soil level to top of plant plane*).—About 60 cm.

*Area of spread.*—About 100 cm.

*Vigor.*—Vigorous.

*Branching habit.*—Freely basal branching; clumping.

*Stems.*—Diameter: About 4 mm. Internode length: About 15 cm. Texture: Sparsely covered with very short (0.5 to 1 mm) grayish-white hairs. Color: Green, 143B to 144B.

*Foliage description.*—Leaves simple, opposite, generally symmetrical, durable and long persisting. Length: About 6.5 cm. Width: About 9 cm. Shape: Palmately divided. Apex: Acute. Base: Sagittate. Margin: Deeply serrated to incised. Texture: Both surfaces with very short, rough hairs; pubescence on lower surface only at the veins. Color: Young and mature foliage, upper surface: 137A to 137B to 138A. Young and mature foliage, lower surface: 137D to 138B. Venation, upper surface: 144B to 145A. Venation, lower surface: 137D to 138B. Petiole: Length: Lower leaves: about 16 cm. Upper leaves: About 8 cm. Diameter: About 2 mm. Color: 144B to 145A. Stipules: Two at each internode; triangular; about 1 by 1.7 cm; transparent, close to 151A.

Flower description:

*Flower type and habit.*—Single violet flowers with purple veins and light lavender centers arranged in pairs; flowers flat and face upward and outward. Flowers self-cleaning. Flowering continuous.

*Natural flowering season.*—Flowering occurs during the summer from mid-June to mid-August in Warmond, The Netherlands.

*Quantity.*—About 12 flowers and flower buds per stem; on mature plants, about 200 flowers and flower buds are typical.

*Fragrance.*—None detected.

*Flower longevity on the plant.*—About 3 days depending on weather conditions.

*Flower size.*—Diameter: About 4.9 cm. Height (depth): About 1.5 cm.

*Flower buds, about one day before opening.*—Length: About 1.5 cm. Diameter: About 1 cm. Shape: Ovate. Color: 89A.

*Petals.*—Arrangement: Five-parted; rotate. Length: About 2.3 cm. Width: About 2.1 cm. Shape: Broadly obovate to obcordate. Apex: Rounded to retuse. Margin: Entire. Texture: Smooth; short white hairs at base. Color: When opening, upper surface: 93B; veins, 82A; base, 85A. When opening, lower surface: 88B; veins, 83A. Opened flower, upper surface: 93B; veins, 83A; base, 85A. Violet color fades to 90B to 90A with subsequent development. Opened flower, lower surface: 88B; veins, 83A.

*Calyx.*—Calyx length: About 5 mm. Calyx width: About 4.9 cm. Sepal arrangement: Five, rotate. Sepal shape: Ovate. Sepal apex: Acute. Sepal margin: Entire. Sepal texture: Smooth; sparsely covered with white hairs. Sepal color: Upper surface: 137C, glossy. Lower surface: 141C.

*Peduncle.*—Angle: Upright to about 55° to stem. Strength: Moderate to strong. Length: About 5 cm. Color: 145A and 182C.

*Reproductive organs.*—Stamens: Stamen number: Ten. Anther shape: Ovate to oblong; dorsifixed. Anther length: About 3 mm. Anther color: Black. Pollen amount: Moderate to scarce. Pollen color: Cream. Pistils: Pistil number: Five. Stigma color: 187A. Style length: About 3 mm. Style color: 187B. Ovary color: 143B to 143C.

*Seed.*—Seed production has not been observed.

Disease resistance: Resistance to pathogens common to Geraniums has not been observed.

It is claimed:

1. A new and distinct cultivar of Geranium plant named 'Jolly Bee', as illustrated and described.

* * * * *

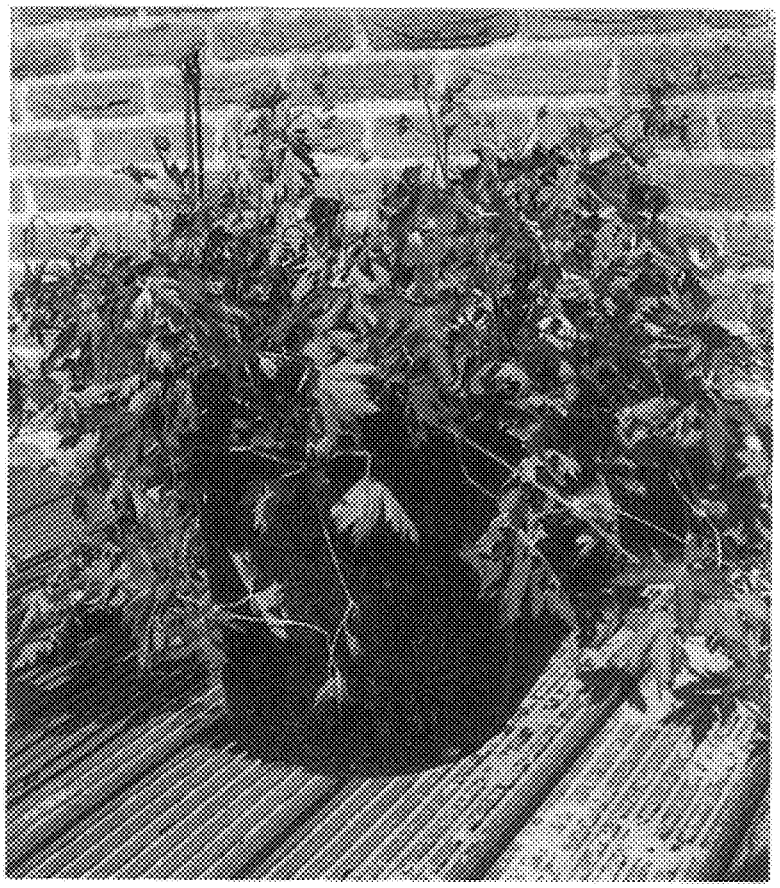
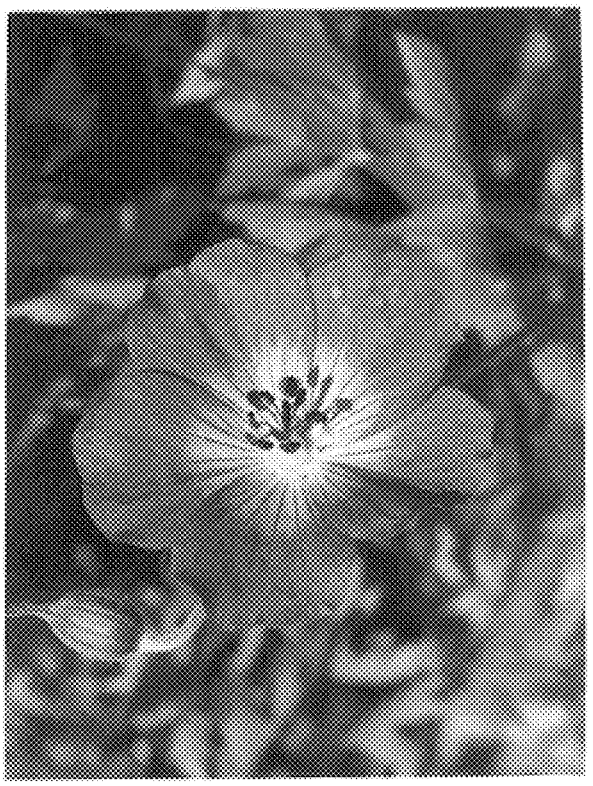

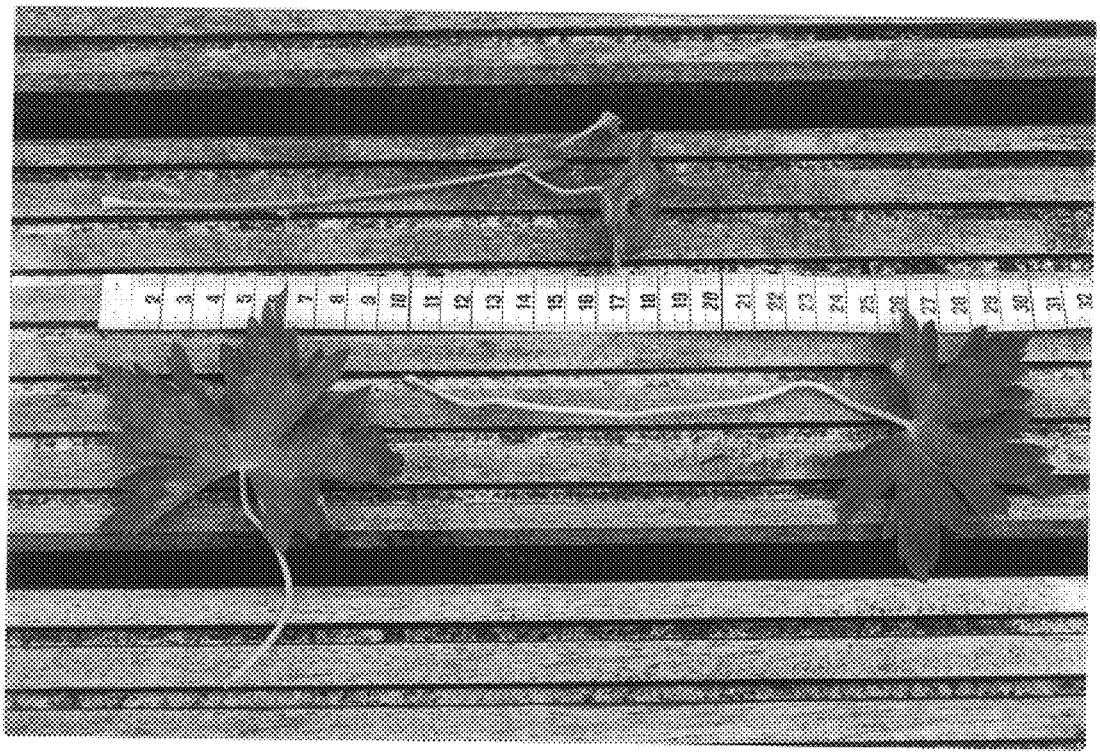
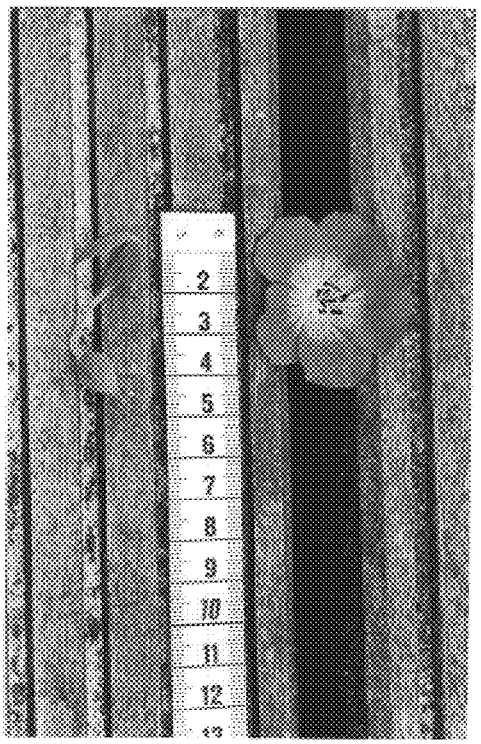
2
3
4
5
6
7
8
9
10
11
12